(12) United States Patent
Sinn et al.

(10) Patent No.: US 8,901,502 B2
(45) Date of Patent: Dec. 2, 2014

(54) DEVICE FOR DETERMINING A PARAMETER OF A MEDIUM

(71) Applicant: KROHNE Optosens GmbH, Neuss (DE)

(72) Inventors: Gert Sinn, Berlin (DE); Thomas Fritsch, Moenchengladbach (DE)

(73) Assignee: KROHNE Optosens GmbH, Neuss (DE)

( * ) Notice: Subject to any disclaimer, the term of this patent is extended or adjusted under 35 U.S.C. 154(b) by 0 days.

(21) Appl. No.: 13/751,613

(22) Filed: Jan. 28, 2013

(65) Prior Publication Data

US 2014/0097347 A1    Apr. 10, 2014

(30) Foreign Application Priority Data

Oct. 4, 2012  (DE) .......................... 10 2012 019 433

(51) Int. Cl.
*G01T 1/20* (2006.01)
*G01N 21/64* (2006.01)

(52) U.S. Cl.
CPC .............. *G01N 21/64* (2013.01); *B01L 2300/18* (2013.01); *B01L 2300/1822* (2013.01)
USPC .......................... 250/364; 250/370.13; 378/62

(58) Field of Classification Search
CPC .................... B01L 2300/1822; B01L 2300/18; G01N 21/64
USPC ................................ 250/364, 370.13; 378/62
See application file for complete search history.

(56) References Cited

U.S. PATENT DOCUMENTS

| 6,288,415 B1 | 9/2001 | Leong et al. |
| 7,088,456 B2 | 8/2006 | Germanenko et al. |
| 7,776,584 B2 | 8/2010 | Richmond et al. |
| 8,083,786 B2 | 12/2011 | Gafni et al. |
| 8,293,527 B2 | 10/2012 | Richmond et al. |
| 2007/0158574 A1* | 7/2007 | Petrillo et al. ........... 250/370.13 |
| 2010/0282982 A1 | 11/2010 | Schreiber et al. |
| 2011/0280369 A1* | 11/2011 | Nishino et al. .................. 378/62 |
| 2012/0243182 A1 | 9/2012 | Campbell et al. |

FOREIGN PATENT DOCUMENTS

| DE | 31 47 295 A1 | 6/1983 |
| DE | 20 2004 008 875 U1 | 9/2004 |
| DE | 20 2005 010 699 U1 | 10/2005 |
| DE | 20 2006 018 202 U1 | 4/2007 |
| DE | 20 2008 014 236 U1 | 3/2009 |
| DE | 20 2010 017 348 U1 | 1/2012 |
| DE | 10 2010 043 083 A1 | 5/2012 |
| DE | 10 2010 050 754 A1 | 5/2012 |

* cited by examiner

*Primary Examiner* — David Porta
*Assistant Examiner* — Abra Fein
(74) *Attorney, Agent, or Firm* — Roberts Mlotkowski Safran & Cole, P.C.; David S. Safran

(57) ABSTRACT

A device (1) is provided for determining at least one parameter of a medium which has a sensor device (2) and an electronic device (3). To provide such a device with a cooling system for at least a portion of its components, the sensor device (2) and/or the electronic device (3) are arranged at least partly in at least one inner space (4, 5) of a housing (6). A passage (7) borders the inner space (4, 5) and a cooling chamber (8) through which a cooling medium can flow is arranged in proximity of the passage (7).

5 Claims, 2 Drawing Sheets

DEVICE FOR DETERMINING A PARAMETER OF A MEDIUM

BACKGROUND OF THE INVENTION

1. Field of the Invention

The invention relates to a device for determining at least one parameter of a medium with at least one sensor device and at least one electronic device. The medium is, for example, a liquid or a suspension or a component of a liquid or a solution. The parameter is, for example, the protein content of a medium containing milk determined by measuring the fluorescence of the medium.

2. Description of Related Art

An exemplary device for measuring the fluorescence of a medium, in order, for example, to determine the protein content of a medium containing milk is described in the German Application DE 10 2009 020 252 A1 and corresponding U.S. Patent Application Publication 2010/0282982 A1. In the prior art, a variety of other devices for the determination of characteristic or process parameters such as level, flow rate, density, viscosity, etc. of media are known. Measuring devices used for determination are often built with a modular construction or at least have a structured design. Thus, there are usually components or units that are specific to the measuring principle and elements, which are essentially independent from them. Elements of energy supply, e.g., belong to the latter group, for conversion of the primary measuring signals, for example, into signals transferable via field buses, etc. Therefore, a substantial separation between a sensor device and an electronic device is advisable. Where appropriate, the sensor device consists of only one component interacting with the media.

Typically, the sensor device and the electronic device and any other components are housed in a housing, which allows for protection against process conditions. One problem with the interior space essentially closed by the housing and the electrical parts and components mostly generating heat is, however, that many of the components (including, in particular, components for optical applications) require a constant temperature in order to operate stably. Therefore, in particular, the heat that is generated by the parts or components must by suitably dissipated.

SUMMARY OF THE INVENTION

A primary object of the present invention is to provide a device for determining at least one parameter of a medium, which has a cooling system for at least a portion of its components.

The object indicated above is initially and essentially met according to the invention by the device described herein in which the sensor device and/or the electronic device is/are arranged at least partially in at least one interior space of a housing. Here, a passage is adjacent to the at least one interior space and at least one cooling chamber that can have through-flow of at least one cooling medium is arranged close to the passage. Active cooling is provided in the device according to the invention, in that a cooling medium is passed through a cooling chamber in the housing of the device. In one design, at least one temperature sensor is provided in the housing of the device for optimum cooling. In one design, the cooling chamber is located along a longitudinal axis of the housing, in particular at least partly at a height at which the passage is found. In one design, the passage is, in particular, at least partially coaxially surrounded by the cooling chamber.

Overall, the device according to the invention has a sensor and electronic device. At least the sensor or electronic device, at least in part, is located in a housing with at least one interior space. At least one passage is provided adjacent to the interior space, which has a cooling chamber close by that can have through-flow of a cooling medium. The cooling chamber is a cavity that is at least partially disposed in the housing and which, for example, has water or a gas or gas mixture flowing through it.

Among the components to be stabilized are, for example, LEDs, components of a laser, or photomultiplier or semiconductor detectors.

In one embodiment, the housing has at least a first and a second interior space. Here, the passage is located between the first interior space and the second interior space. The electrical connection between the components or parts of the measuring device located in each interior space is preferably implemented through the passage.

In one design, the electronic device is located in the first interior space and the sensor device in the second interior space. Alternatively, one part of the sensor device is found in the first interior space and one part of the sensor device is found in the second interior space. The same is implemented, alternatively, for the electronic device, which, in one design, is partially placed in the first and second interior spaces and components thereof are interconnected through the passage.

In one design, at least one electrical connection is arranged in the passage between the sensor device and the electronic device. For example, a plug-in connection is lead through, for example, a tunnel-like passage. Alternatively or additionally, electrical leads or pins are provided for mutually connecting the sensor device and the electronic device. If parts of either the sensor or electronic device are located in the at least two interior spaces, the passage correspondingly allows for the arrangement of connections between the components or partial components of the electronic or sensor device.

In one design, the cooling chamber at least partially surrounds the passage in its circumference. The cooling chamber is, therefore, in one design, concentrically positioned around the passage. The cooling chamber is preferably at least partially designed as a hollow cylinder and extends along a predetermined radius around the passage. In an alternative embodiment, the cooling chamber extends also at least partially through the passage. The cooling chamber is, in particular, located near the particularly temperature-sensitive parts or components. Alternatively or additionally, large-scale as possible temperature control is achieved through the shape and arrangement of the cooling chamber. In one design, as few as possible components being as thermally conductive as possible are arranged between components to be cooled or areas in the housing. The housing around the cooling chamber is preferably formed of stainless steel and meanders in one design at least in a partially meandering shape around the passage.

In one design, at least one cooling element is provided adjacent to the cooling chamber. In one design, such a cooling element enhances the cooling effect of the cooling solution. In a supplementary or alternative design, cooling using the cooling chamber is downstream to the cooling using the cooling element, wherein the heat generated by the cooling element is removed by means of this secondary cooling in one design. In one design, in particular, multiple cooling elements are provided preferably in the vicinity of the cooling chamber. In one design, at least one cooling element is a Peltier element.

In one design, at least one cooling element is provided axially along a longitudinal axis of the housing on each of both sides of the cooling chamber—that is, in front of and behind the cooling chamber axially. This is especially useful in that temperature sensitive components on both sides of the cooling chamber are cooled by means of the cooling elements and that the cooling elements are cooled again together by the cooling solution in the cooling chamber.

In one design, the housing is configured in multiple parts, and in particular, at least two parts.

In one variation, the cooling chamber is essentially completely housed in a part of the housing.

In an alternative design, the cooling chamber is formed by structures of a first housing part surrounding at least an interior space and by structures in at least one further housing part. The cooling chamber is obtained therefore by a joining of the two housing parts. The structures are, for example, recesses, elevations, etc. that are particularly adapted to correspond with one another.

In a further design, the cooling chamber is obtained using structures that belong to at least three housing parts.

In one design, the second interior space is located in a second housing part. Thus, the passage is located between the first and the second interior space and, thereby, between the first and the second housing part, each of which comprising or forming the two interior spaces.

In an alternative design, the passage is adjacent to an interior space and ends outside of the housing.

In one design, the housing has an essentially disk-shaped separating element as a component that forms at least one section of the passage. In one design, the separating element is located between the two interior spaces of the housing.

That the housing is made of multiple parts, and for example, that there is a separating element, make access to components built in the housing possible by means of detachable assembly. In particular, a cooling chamber, which is obtained by the interaction of several housing parts—particularly being releasably interconnected—make simple and complete access possible even during operation—i.e., for a measuring device built-in in the process—which can be used, e.g., for cleaning purposes. If the sensor device remains limited in an interior space of a housing part, it is also ensured that the individual components of the sensor device remain aligned to one another, which is of much relevance particularly in the case of optical measurement devices.

In one design, the housing is designed, at least in the region of the passage, essentially rotationally symmetrical and/or circular-cylindrical.

In one embodiment, the sensor device has at least one radiation source and at least one radiation-receiving element. Furthermore, the sensor device is designed for measuring at least the fluorescence of the medium. The nature of the fluorescence measurement and the determination of parameters of the medium from it are based, for example, on the teaching of German Patent Application DE 10 2009 020 252 A1 and corresponding U.S. Patent Application Publication 2010/0282982 A1.

In detail, there are now a variety of options for designing and further developing the device according to the invention. In this regard, reference is made to the following description of embodiments in conjunction with the accompanying drawings.

DETAILED DESCRIPTION OF THE INVENTION

Figure 1:
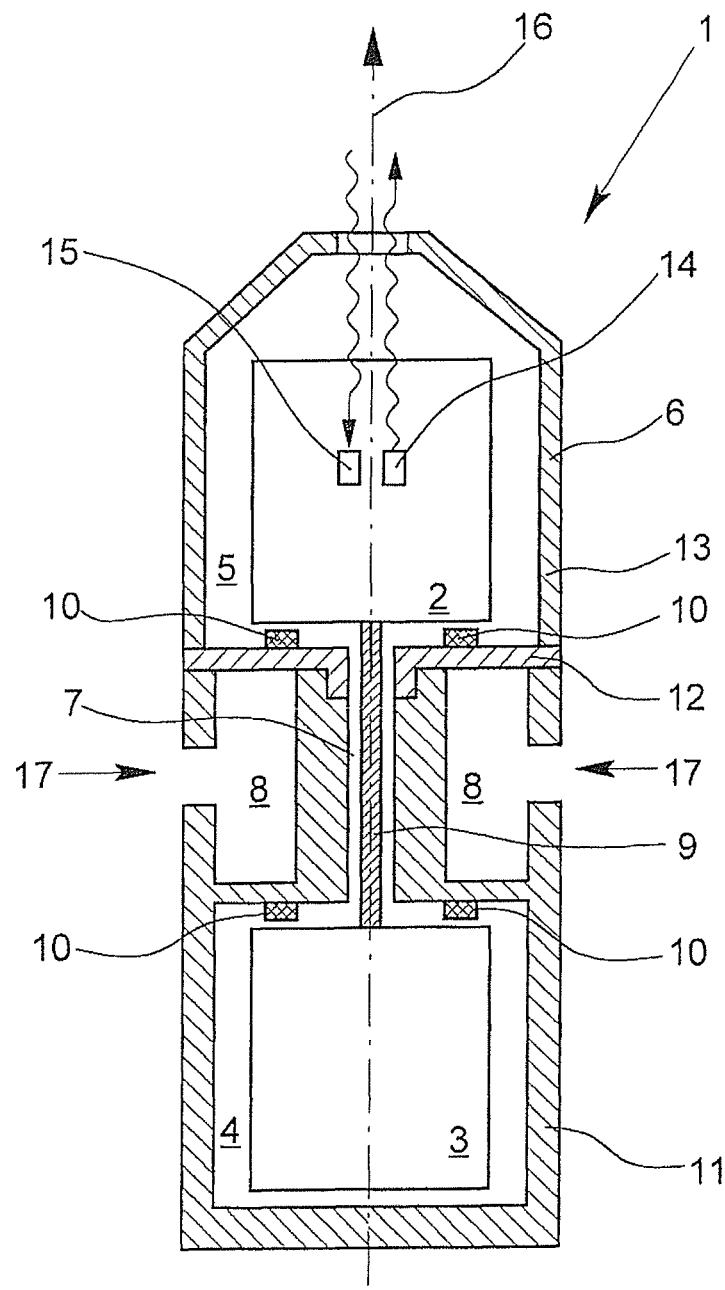
FIG. 1 is a cross-sectional view of a first embodiment of a device for measuring the fluorescence of a medium and FIG. 2 is a cross-sectional view of a cooling chamber element of a second embodiment.

The schematically illustrated device 1 in FIG. 1 is used to measure the fluorescence for determining at least one parameter of a medium. For this, the illustrated device 1 has a sensor device 2 and an electronic device 3. The sensor device 2 comprises also electronic components and elements, but mainly only those components that are used for actual measurement. The electronic device 3 comprises more generally required components (such as, e.g., for energy supply, the control of the sensor components, further processing of measurement data, etc.), which are more independent from the measuring principle used in the device 1.

To protect the elements of the sensor device 2 and the electronic device 3 against process and environmental conditions, the electronic device 3 is located in a first interior space 4, and the sensor device 2 in a second interior space 5 of the housing 6 completely surrounding the device 1. The housing 6 is designed, in particular, having multiple parts, i.e., of a plurality of components/elements, which, for example, are detachably connected together via screw connections.

A passage 7 for connecting the sensor device 2 and the electronic device 3 or between the components thereof is located in the housing 6. A cooling chamber 8 is provided in this—essentially flange-like—transition region of the housing 6 between the two interior spaces 4, 5, and which has a coolant flowing through it, e.g., water or a gas or gas mixture.

The illustrated housing 6 is rotationally symmetrical and is, in particular, cylindrically designed at the height of the passage 7 or the cooling chamber 8. In the embodiment shown, the cooling chamber 8 circumferentially surrounds the passage—as a hollow cylinder—and hence also the electrical connection 9 in the passage 7. The electrical connection, for example, is an at least partially cast-in, plug-in contact connected to electrical leads, which establishes the electrical contact between the sensor device 2 and the electronic device 3.

An active cooling system is made possible by the cooling chamber 8, which, in particular, discharges heat generated by the cooling elements 10 arranged near the cooling chamber 8. The cooling elements 10 are, for example, Peltier elements, which are used for the active cooling of elements of the sensor device 2 or the electronics device 3. Downstream from the cooling elements 10, and thus, a secondary cooling system, the cooling medium is lead through the cooling chamber 8 and thereby brings about the cooling of the cooling elements 10—acting as primary cooling system.

The multi-part—here, in particular, three-part—housing 6 has a first housing part 11, which surrounds the first interior space 4 and contains the electronic device 3, a substantially disk-shaped separating element 12 and a second housing part 13, which has the sensor device 2 in the second interior space 5. In another embodiment, the separating element 12 and the first housing part 11 or the second housing part 13 are formed integrally.

The separating element 12 and the first housing part 11 each have structures (recesses, elevations, etc.), which together define the cooling chamber 8. The separating member 12 forms, in particular, also a part of the passage 7 and closes quasi as a cover the cooling chamber 8 in the direction of the second housing part 13.

At least one radiation source 14 and a beam-receiving element 15 are provided for the actual measurement as part of the sensor device 2, which radiate electromagnetic waves, here, towards a window of the housing 6, or after interaction with medium receive electromagnetic waves. For example, the medium can be characterized in more detail from the detection of fluorescence radiation emitted from the medium or a component of the medium. This occurs here especially inline, i.e., without taking a sample from the process. For further details of measurement, reference is made, as an example, to the published patent application DE 10 2009 020 252 A1 and corresponding U.S. Patent Application Publication 2010/0282982 A1.

The cooling elements 10 provided for the primary cooling of the components of the sensor device 2 or the electronic device 3 are located axially along the longitudinal axis 16 of the housing 6 and behind the cooling chamber 8. The heat from the cooling elements 10 is discharged by the cooling medium, which is supplied or discharged through the connection access 17, and thus, flows through the cooling chamber 8. For this, for example, a pump or the like is connected via hoses for the flow of the cooling medium.

Figure 2:
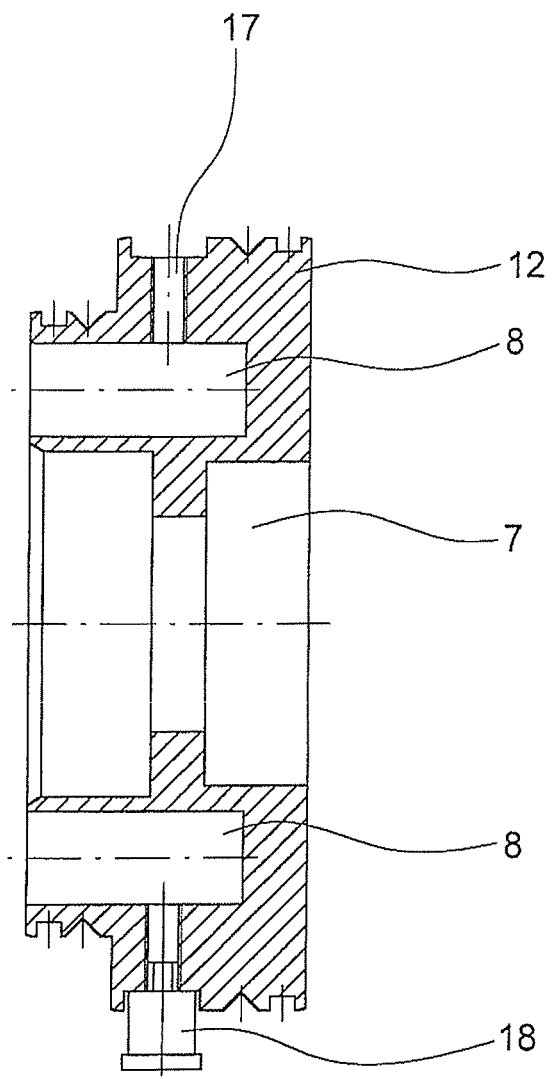

A separating element 12 of an alternative embodiment is shown in FIG. 2. There, the recesses for the cooling chambers 8 to have coolant flowing through them are located in the separating element 12 and not—as shown in the variation of FIG. 1—in the first housing part. The cooling chambers 8, which are arranged around the passage 7, border the connection accesses 17. The—here graphically lower—connection access 17 is provided with a fitting 18, which allows for the connection of a hose for the coolant.

What is claimed is:

1. A device for determining at least one parameter of a medium, comprising:
   a housing having at least a first inner space, a second inner space, and a passage located between said first inner space and said second inner space,
   said housing being a three-part housing and having a first housing part surrounding said first inner space, a second housing part surrounding said second inner space, and a separating element forming at least a part of said passage,
   at least one sensor device arranged only within said second inner space and
   at least one electronic device arranged only within said first inner space,
   at least one electrical connection connecting said sensor device with said electronic device and arranged in said passage,
   wherein, at least one cooling chamber through which at least one cooling medium is flowable is arranged circumferentially surrounding said passage,
   said cooling chamber being formed by structures of said first housing part and said separating element,
   said cooling chamber having an access for supplying the at least one cooling medium and an access discharging said at least one cooling medium,
   wherein at least one cooling element is located within one of said first housing part and said second housing part adjacent to said cooling chamber, and
   wherein said at least one cooling medium is able to remove heat generated by said at least one cooling element as if flows through said cooling chamber.

2. The device according to claim 1, wherein the sensor device comprises at least one radiation source and at least one radiation-receiving element, wherein said at least one radiation source and said at least one radiation-receiving element are located within said second housing part, and wherein the sensor device is adapted for measuring at least fluorescence of the medium.

3. The device according to claim 1, wherein said at least one cooling element is a Peltier element.

4. The device according to claim 1, wherein said at least one cooling element is located within said first inner space.

5. The device according to claim 1, wherein said at least one cooling element is located within said second inner space.

* * * * *